United States Patent [19]

Leonard

[11]  4,290,968

[45]  Sep. 22, 1981

[54] PREPARATION OF POLYISOCYANATES FROM POLYCARBAMATES

[75] Inventor: John J. Leonard, Springfield, Pa.

[73] Assignee: Atlantic Richfield Company, Los Angeles, Calif.

[21] Appl. No.: 171,522

[22] Filed: Jul. 23, 1980

[51] Int. Cl.$^3$ ............................................. C07C 118/00
[52] U.S. Cl. ................................... 260/453 P; 560/25
[58] Field of Search ....................... 260/453 P; 560/25

[56] References Cited

U.S. PATENT DOCUMENTS

| | | | |
|---|---|---|---|
| 2,946,768 | 7/1960 | Klauke et al. | 560/25 |
| 3,919,279 | 11/1975 | Rosenthal et al. | 260/453 P |
| 3,962,302 | 6/1976 | Rosenthal et al. | 260/453 P |
| 4,146,727 | 3/1979 | Shawl et al. | 560/25 |
| 4,162,362 | 7/1979 | Shawl | 560/25 |
| 4,172,948 | 10/1979 | Shawl | 560/25 |

*Primary Examiner*—Dolph H. Torrence
*Attorney, Agent, or Firm*—Delbert E. McCaslin

[57] ABSTRACT

In the process of producing polyisocyanates by
(a) condensing an alkyl-N-phenylcarbamate having 1 to 3 carbons in the alkyl moiety in the presence of an acid to produce condensate containing diphenylmethane dicarbamates and polymethylene polyphenyl carbamates with by-product N-benzyl compounds, rearranging said N-benzyl compounds in said condensate with acid catalyst to obtain a pyrolysis feed mixture containing diphenylmethane dicarbamates, polymethylene polyphenyl carbamates and 0.02 to 1.0 percent by weight of amine impurities as $NH_2$ groups, and
(b) thermally decomposing the carbamate moieties in the pyrolysis feed mixture to isocyanate moieties to produce polyisocyanates, the improvement comprises increasing the percent isocyanate content of said polyisocyanates by prior to step (b) converting any amine salt by-products in said pyrolysis feed mixture to free amine by-products by contacting the mixture with a weakly basic tertiary amine anion exchange resin and removing any free amine by-products by contacting the feed mixture with a strongly acidic sulfonated polyaromatic ion exchange resin whereby the amine impurity in the pyrolysis feed mixture is reduced to less than 0.001 percent by weight as $NH_2$ groups.

3 Claims, No Drawings

PREPARATION OF POLYISOCYANATES FROM POLYCARBAMATES

FIELD OF THE INVENTION

The present invention relates to an improvement in the process for the preparation of polyisocyanates from polycarbamates (polyurethanes). The improvement relates to removal of amine and amine salts from the polyurethane prior to its pyrolytic decomposition to polyisocyanate which results in higher levels of isocyanate content.

BACKGROUND OF THE INVENTION

Polymeric aromatic carbamic acid esters (polyurethanes) such as diphenylmethane dicarbamates and the related higher homologs, polymethylene polyphenyl carbamates, have become increasingly important products particularly, for use in the preparation of the commercially valuable diphenylmethane diisocyanates and mixtures of diisocyanates and the polyisocyanates by the decomposition of such polymeric aromatic carbamic acid esters in a suitable solvent as shown in Rosenthal et al., U.S. Pat. Nos. 3,962,302 and 3,919,279.

A proposed prior art process for the preparation of polymeric aromatic carbamic acid esters (polyurethanes) is disclosed in Klauke et al, U.S. Pat. No. 2,946,768 and involves the condensation of aryl carbamic acid esters with carbonyl compounds in a dilute aqueous acid condensation medium. However, in such process the carbonyl compound such as formaldehyde tends to react at the nitrogen of the carbamate to produce along with desired polyurethanes, varying amounts, i.e., generally between 15 percent and 50 percent by weight, of undesirable (alkoxycarbonyl)-phenylaminomethylphenyl compounds which includes the various dimers, trimers, tetramers, etc. of such compounds (also referred to herein as "N-benzyl" compounds). Attempts to prepare mono or diisocyanates and polyisocyanates or to otherwise use the mixture containing the undesired N-benzyl compounds, which cannot be converted to an isocyanate by pyrolysis, and polyurethanes presents many problems. However, the undesired N-benzyl compounds may be catalytically rearranged to a desired polyurethane in accordance with the teachings of Shawl et al, U.S. Pat. No. 4,146,727. Accordingly, a product mixture from a condensation as disclosed in aforementioned U.S. Pat. No. 2,946,768 containing diurethanes and polyurethanes, N-benzyl compounds, unreacted alkylphenylcarbamates and other by-products such as amines may be contacted at temperatures of from about 50° C. to 170° C. with a protonic acid medium having a strength at least equal to a 75 percent sulfuric acid such as concentrated sulfuric acid or an acid medium comprising a Lewis acid having a concentration of at least 0.5 percent by weight based on the total reaction mixture, while maintaining a minimum amount of water in the system, to catalytically convert or rearrange said N-benzyl compounds.

Shawl, U.S. Pat. No. 4,172,948, discloses a similar rearrangement of N-benzyl compounds may be achieved by use of anhydrous hydrogen chloride under super atmospheric pressure.

Condensation of aryl carbamic acid esters with formaldehyde may also be conducted with organic sulfonic acids. Shawl, U.S. Pat. No. 4,162,362, teaches that condensation in the presence of an organic sulfonic acid eliminates formation of N-benzyl compounds and suppresses certain other undesirable side reactions.

SUMMARY OF THE INVENTION

The acid catalyzed condensation of N-aryl carbamates and the acid rearrangement of N-benzyl compounds produce some hydrolysis of urethane groups to amino groups. Thus, for example, in the acid catalyzed condensation of ethyl-N-phenyl carbamate with formaldehyde some hydrolysis of the urethane (carbamate) groups occurs and the amino compound would thus correspond to the carbamate from which it is derived and may amount to 0.02 to 1.0 percent by weight of amine impurity as $NH_2$ groups. Although hydrolysis of the starting ethyl-N-phenyl carbamate to aniline can occur, the most troublesome amines have methylene bridged phenyl moieties with each phenyl having a carbamate or amino substituent.

By-product amino compounds may be present in the condensation-rearrangement product as free amines and as amine/acid salts. It has been discovered that when the by-product amines and amine salts accompany the condensation-rearrangement product to its pyrolytic decomposition to polyisocyanate, a significant detrimental effect results. For example, the amines and amine salts can react with isocyanate groups as they form to produce ureas or biurets. Additionally, such undesirable ureas might at elevated temperatures catalyze isocyanate reactions to produce other unwanted by-products such as carbodiimides and isocyanurates.

It has now been discovered that by amine removal prior to pyrolysis those detrimental effects may be avoided. Amine removal is achieved by contacting the condensation-rearrangement product first with a weakly basic tertiary amine ion exchange resin and then with a strongly acidic sulfonated polyaromatic ion exchange resin. Alternatively, the product may be contacted by a bed of a mixture of both types of ion exchange resins. That treatment removes both amines and amine salts from the condensation-rearrangement product.

Accordingly it is an object of this invention to provide a process with increased yield of polyisocyanates from polyurethanes by removing amines and amine salts from the polyurethane prior to pyrolytic decomposition.

It is another object of this invention to provide a process for producing polyisocyanates with an increased percentage of isocyanate group content.

These and other objects and advantages of this invention will become apparent from the description of the invention which follows and from the claims.

DESCRIPTION OF THE INVENTION

Condensation of alkyl-N-aryl carbamates with formaldehyde is known to yield polyfunctional carbamates with alternating methylene moieties and N-aryl carbamate moieties as shown by the formula

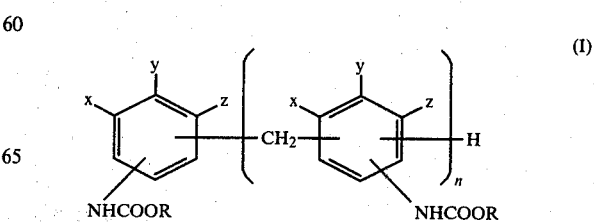

wherein x, y and z when the same are each hydrogen or when different x, y and z may be hydrogen, alkyl having 1–3 carbon atoms, —NHCOOR, —CH$_2$ArNHCOOR, or —N(COOR)CH$_2$Ar;

n is at least one;

R is alkyl having 1–3 carbon atoms and

Ar is phenyl which is unsubstituted or substituted with alkyl having 1–3 carbon atoms.

Production of polyfunctional carbamates by acidic condensation of a monofunctional N-aryl carbamate with formaldehyde results in a small amount of the carbamate functional groups being hydrolyzed to amino groups as shown by the reaction

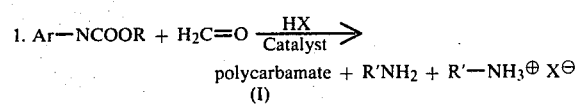

polycarbamate + R'NH$_2$ + R'—NH$_3^\oplus$ X$^\ominus$
(I)

wherein Ar and R are as defined above, the polycarbamate is of formula (I) above and R' is an organic moiety containing methylene bridged aromatic rings bearing carbamate or other amino substituents. In order for the process of pyrolyzing dicarbamates and polymethylene polyphenyl carbamates (urethanes) to be a viable process it is imperative, because of the high temperatures required for such pyrolysis and the inherent instability of isocyanate groups produced at high temperatures, that the urethanes be of the highest possible purity and thus provide yields of isocyanate (NCO) groups of at least 95 percent. The aromatic amine by-products which are formed by hydrolysis of the urethane groups during acid condensation and rearrangement reactions are a particularly detrimental class of impurities. As much as 1 to 2 percent of the urethane groups may be hydrolyzed, resulting in from about 0.02 to 1.0 percent by weight of amine impurities as NH$_2$ groups in the reaction product. In urethane pyrolysis the amines can react with the formed isocyanates to give ureas which may also form biurets. The amines, or products derived therefrom, can act catalytically to form other undesirable by-products such as carbodiimides and isocyanurates.

As shown by reaction 1 above, the amine by-product may be present as the free amine or as the amine salt of an acid catalyst from the condensation-rearrangement process for producing the polycarbamate. Such acids, represented by HX in reaction 1. above, are known in the art and include strong mineral acids such as sulfuric acid.

Both the free amine and the amine salt can be effectively removed from the polycarbamate condensation-rearrangement reaction product by contacting the reaction product in solution with a mixed bed (monobed) of a weakly basic tertiary amine ion exchange resin and a strongly acidic sulfonated polyaromatic ion exchange resin. That treatment results in a urethane solution with less than 0.001 weight percent of amine impurity as NH$_2$ groups. The sulfonic acid acidic ion exchange resin alone would be effective to remove the free amine but would not effectively remove amine salts. Most of the amine by-product would be present in the salt form because the condensation-rearrangement reaction is acid catalyzed. Thus both types of resins are required for complete amine by-product removal.

By using a mixed bed of a basic tertiary amine ion exchange resin together with an acidic sulfonated polyaromatic ion exchange resin, the following reactions occur with the undesirable amine by-products:

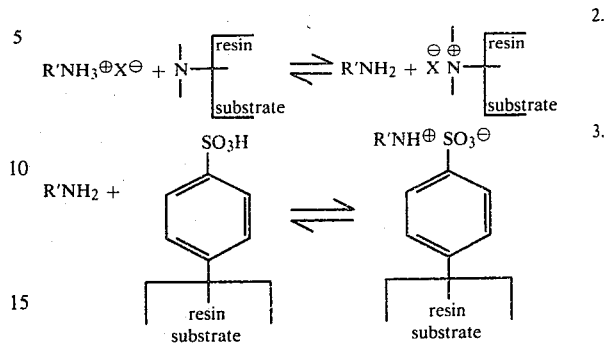

The basic ion exchange resin converts the by-product amine salt to free by-product amine and concurrently removes acid HX by salt formation with the basic ion exchange resin as shown in reaction 2. The free amine by-product resulting from reaction 2. as well as any other free amine reacts with the acidic sulfonated polyaromatic ion exchange resin as shown in reaction 3. Because the amine is ionically bonded to the resin, it is effectively removed from the condensation-rearrangement reaction product.

Although use of both acid and basic ion exchange resins mixed in a single bed (monobed) is preferred, a two step sequential treatment with an individual bed of each resin may be employed. When using individual beds, it is imperative to contact the condensation-rearrangement reaction product first with the basic ion exchange resin to effect reaction 2. prior to contact with the acid ion exchange resin (reaction 3.). It is readily apparent that reversal of the order would defeat the complete removal of amine by-product.

The ion exchange resins suitable for this invention are themselves well known. A particularly suitable basic tertiary amine ion exchange resin is sold by Rohm and Haas Company under the trademark Amberlyst A-21 which has a density of about 37 to 42 lbs/ft.$^3$, a minimum anion exchange capacity of 4.2 meq./g. of dry resin, a surface area of about 30 to 40 m$^2$/g, and an average pore diameter of about 900 to 1300 Angstrom units. Suitable acidic resins are any sulfonated polystyrene type resin and a particularly suitable acidic resin is sold by Rohm and Haas Company under the trademark Amberlyst 15 which has a bulk density of approximately 595 g/l., a hydrogen ion concentration of approximately 4.9 milliequivalents/g. dry, a surface area of from about 40 to 50 m$^2$/g. and an average pore diameter of from about 200 to 600 Angstrom units. The amount of ion exchange resin used is of such a magnitude that the weight ratio of condensation-rearrangement product treated to acidic resin should be between 0.1 and 1.0 and the weight ratio of product treated to basic resin should be between 0.05 and 1.0.

Both the condensation-rearrangement reaction product and the ion exchange resins must be essentially dry since the presence of moisture would result in carbamate hydrolysis catalyzed by the resins. Accordingly, a nonaqueous solvent may be used to prepare the resin bed and as solvent for the condensation rearrangement reaction product treated. Suitable solvents are nitrobenzene, toluene, xylene, benzene, alcohols, ethers and ketones. Nitrobenzene, ethanol, dimethyl ether and dimethyl ketone are especially suitable. Nitrobenzene is preferred inasmuch as it is frequently used as the reaction solvent in the condensation-rearrangement reaction.

The following examples are provided to illustrate the process in accordance with the principles of this invention but are not to be construed as limiting the invention in any way except as indicated by the appended claims.

EXAMPLE 1

A condensation-rearrangement product was prepared according to the following procedure (see U.S. Pat. No. 4,146,727): A condensation product from the reaction of ethylphenylcarbamate with a 30 percent aqueous formaldehyde solution and 37 weight percent hydrochloric acid in water was prepared according to Example 2 of U.S. Pat. No. 2,946,768 and contained approximately 33 percent unreacted ethylphenylcarbamate, 38 percent diphenylmethane dicarbamates (2,4' and 4,4'-isomers), 4 percent triurethanes, 15 percent N-benzyl compound dimer (2 and 4-[(ethoxycarbonyl) phenylaminomethyl]phenylcarbamic acid, ethyl ester), 8 percent N-benzyl compound trimers such as 4[(ethoxycarbonyl)phenylaminomethyl]-2,4'-methylenebis(-phenylcarbamic acid)diethyl ester and a small amount of other unidentified by-products. Eighteen g. of the condensation reaction product along with 18 g. of nitrobenzene solvent and 6.0 g. of 96.4 weight percent sulfuric acid were charged to a reaction flask and heated at 80° C. for 30 minutes. After completion of the reaction and acid extraction, analysis of the product showed 100 percent conversion of the N-benzyl compound dimers and trimers to the desired methylene group bridged aromatic di- and triurethane compounds. After removal of solvent the reaction mixture contained 0.10 wt. % total $NH_2$ groups. Anhydrous Amberlyst 15 resin (22.8 g.) were slurried with nitrobenzene and charged to a one inch i.d. glass column 2.5 ft. long. Anhydrous Amberlyst A-21 (60.8 g.) were slurried with nitrobenzene and charged to the same column. After backflushing with nitrobenzene, four bed volumes of nitrobenzene were passed through at a rate of four bed volumes per hour. At this point, a solution containing 50 wt.% condensation-rearrangement product in nitrobenzene (17 g. product+18 g. nitrobenzene) was added to the column and eluted with four bed volumes of nitrobenzene. The eluent was distilled to remove nitrobenzene giving 18 g. of treated product as a residue.

The treated condensation-rearrangement product was pyrolyzed to form a polymeric isocyanate as follows. Eighteen g. of product was dissolved in 1 l. of diphenyl ether containing 7 ppm aluminum acetylacetonate. This solution was added to a 2 l. round bottom flask equipped with a nitrogen sparger, heater, and 1 ft. Vigeraux column and overhead condenser. The solution was heated to 250° C. and purged with nitrogen at 1 l./min. After 80 to 100 ml. of overhead were collected, analysis showed no ethanol in the overhead. At this point, the flask was cooled to 130° C. and the diphenyl ether distilled off under vacuum with a final pressure of 0.5–1.0 mm Hg. The isocyanate content of the residue was determined by titration and expressed as wt.% NCO. Untreated condensation-rearrangement product was pyrolyzed in an identical procedure. The results are summarized in Table A below.

EXAMPLE 2

The procedure of Example 1 was repeated except that 50 g. of reaction product were treated in a resin bed contained 50 g. of acidic resin and 80 g. of basic resin. The results are summarized in Table A.

EXAMPLE 2a (Comparison)

To illustrate the importance of the joint use of the acidic and basic resins, Example 2 was repeated but the basic resin was omitted from the bed. The results in Table A show a higher isocyanate content for Example 2 treated product than for Example 2a.

EXAMPLE 3

The procedure of Example 1 was repeated except ethanol was used in place of nitrobenzene as solvent and 21.8 g. of product contacted a monobed of 15.2 g. acid resin with 40.5 g. basic resin at an elution rate of 3. The results are summarized in Table A.

EXAMPLE 4

The procedure of Example 3 was repeated with 30.0 g. of product being treated. The results are summarized in Table A.

EXAMPLE 5

The procedure of Example 1 was repeated with toluene replacing nitrobenzene as solvent and 66 g. of reaction product was contacted by a monobed containing 30 g. acidic resin and 80 g. basic resin. The results are summarized in Table A.

EXAMPLE 5a

The procedure of Example 5 was repeated except the monobed contained 190 g. acidic resin and 1310 g. basic resin. The results are summarized in Table A.

EXAMPLE 6

The procedure of Example 1 was repeated except that 30 g. of reaction product contacted a monobed containing 15.4 g. acidic resin and 40.5 g. basic resin. The results are summarized in Table A.

EXAMPLE 7

The procedure of Example 6 was repeated except the monobed contained 60 g. acidic resin and 160 g. basic resin. The results are summarized in Table A.

TABLE A

| | Treatment Procedure | | | | Elution[2] | wt. % NCO after |
|---|---|---|---|---|---|---|
| Example | Solvent | g Prod. | g A-15[1] | g A-21[1] | Rate | Pyrolysis |
| 1 | nitrobenzene | 18 | 22.8 | 60.8 | 4 | 30.8 (30.0)[3] |
| 2 | nitrobenzene | 50 | 50.0 | 80.0 | 4 | 29.7 (28.9) |
| 2a | nitrobenzene | 50 | 50.0 | 0.0 | 4 | 29.3 (28.9) |
| 3 | ethanol | 21.8 | 15.2 | 40.5 | 3 | 30.5 (30.0) |
| 4 | ethanol | 30.0 | 15.2 | 40.5 | 3 | 29.2 (27.6) |
| 5 | toluene | 66 | 30.0 | 80.0 | 4 | 30.9 (30.1) |
| 5a | toluene | 66 | 190.0 | 1310.0 | 4 | 31.5 (30.1) |
| 6 | nitrobenzene | 30 | 15.4 | 40.5 | 4 | 30.7 (28.0) |

TABLE A-continued

| | Treatment Procedure | | | | Elution[2] | wt. % NCO after |
|---|---|---|---|---|---|---|
| Example | Solvent | g Prod. | g A-15[1] | g A-21[1] | Rate | Pyrolysis |
| 7 | nitrobenzene | 30 | 60.0 | 160.0 | 4 | 31.5 (28.0) |

[1]Anhydrous wts. of Amberlyst-15 (A-15) and Amberlyst-21 (A-21)
[2]Bed volumes/hour
[3]Value in ( ) obtained on untreated material.

What is claimed is:

1. In the process of producing polyisocyanates by (a) condensing an alkyl-N-phenylcarbamate having 1 to 3 carbons in the alkyl moiety in the presence of an acid to produce condensate containing diphenylmethane dicarbamates and polymethylene polyphenyl carbamates with by-product N-benzyl compounds, rearranging said N-benzyl compounds in said condensate with acid catalyst to obtain a pyrolysis feed mixture containing diphenylmethane dicarbamates, polymethylene polyphenyl carbamates and 0.02 to 1.0 percent by weight of amine impurities as $NH_2$ groups, and (b) thermally decomposing the carbamate moieties in the pyrolysis feed mixture to isocyanate moieties to produce polyisocyanates, the improvement comprises increasing the percent isocyanate content of said polyisocyanates by prior to step (b) converting any amine salt by-products in said pyrolysis feed mixture to free amine by-products by contacting the mixture with a weakly basic tertiary amine anion exchange resin and removing any free amine by-products by contacting the feed mixture with a strongly acidic sulfonated polyaromatic ion exchange resin whereby the amine impurity in the pyrolysis feed mixture is reduced to less than 0.001 percent by weight as $NH_2$ groups.

2. The process of claim 1 wherein a solvent solution of said pyrolysis feed mixture containing said amine and amine salt by-products is passed through a mixed bed of said weakly basic tertiary amine anion exchange resin and said strongly acidic sulfonated polyaromatic ion exchange resin.

3. The process of claim 2 wherein said solvent is selected from the group consisting of nitrobenzene, toluene, xylene, ethanol, dimethyl ether and dimethyl ketone.

* * * * *